United States Patent [19]

Peterson et al.

[11] 4,356,166

[45] Oct. 26, 1982

[54] TIME-RELEASE CHEMICAL DELIVERY SYSTEM

[75] Inventors: Robert V. Peterson, Murray, Utah; James M. Anderson, Cleveland Heights, Ohio; Donald E. Gregonis; Sunj-Wan Kim, both of Salt Lake City, Utah; Jan Feijen, Hengelo, Netherlands

[73] Assignee: University of Utah, Salt Lake City, Utah

[21] Appl. No.: 967,605

[22] Filed: Dec. 8, 1978

[51] Int. Cl.² ................................ A61J 3/00; A61J 3/10; A61K 9/54
[52] U.S. Cl. ................................ 424/19; 424/21; 424/47
[58] Field of Search ..................................... 424/19

[56] References Cited

U.S. PATENT DOCUMENTS

| | | | |
|---|---|---|---|
| 3,639,516 | 2/1972 | Sarfaty et al. | 424/238 |
| 3,950,282 | 4/1976 | Gilbert et al. | 424/19 |
| 4,122,129 | 10/1978 | Casey et al. | 424/19 |

*Primary Examiner*—Elbert L. Roberts
*Attorney, Agent, or Firm*—Trask & Britt

[57] ABSTRACT

A time-release chemical delivery system in which a bioactive compound is attached to a polymeric biodegradable carrier by a hydrolyzable bond is disclosed. The bioactive compound can either be bound directly to the polymer or be attached to the polymer via a spacer group. The composition of the system is particularly effective for delivering medication systemically to a host animal over a prolonged period of time after being surgically implanted or injected subcutaneously. Biodegradable condensation polymers having reactive pendant groups, for example, poly-L-(glutamic acid), or derivatized poly-L-(glutamic acid) are effective as polymeric carriers.

10 Claims, No Drawings

TIME-RELEASE CHEMICAL DELIVERY SYSTEM

The invention was made under a Department of Health, Education and Welfare grant.

BACKGROUND OF THE INVENTION

1. Field

The invention relates to a time release system for releasing a bioactive agent over a prolonged period of time.

2. Prior Art

As indicated in "Controlled Release Polymeric Formulations" by D. R. Paul and W. F. Harris, ACS Symposium Series 33, The American Chemical Society (1976), an active interest has existed in controlled release polymeric formulations since the 1960's. Various systems have been utilized in the past, such as erodable devices wherein a drug or other chemically active agent absorbed into a chemical matrix is released as the matrix is eroded or dissolved.

Other systems involve encapsulation wherein the medicant or active agent is enclosed or encapsulated by a polymeric shell through which the agent diffuses. The diffusion rate through the shell controls the rate of release. A system of this type is disclosed in U.S. Pat. No. 3,577,512.

Naloxone has been chemically attached to a polyhydrazine ficoll polymer according to Pasternak et al, Life Sciences, Vol. 18, pp. 977-982 in an article entitled "Micromolecular Naloxone: A Novel Long-Acting Polymer-Bound Drug". The macromolecular naloxone is injected into its host as a narcotic antagonist.

Allan et al, Chemtech, March 1973, page 177 et.seq., "Pesticides, Pollution and Polymers", describes the attachment of pesticides to water soluble and insoluble polymers, both directly and through the use of a spacer moiety.

OBJECTS OF THE INVENTION

An object of the instant invention is to control the rate of drug release by the application of polymeric systems with varying degrees of hydrophilicity and varying degrees of drug loading.

It is an object of the instant invention to provide a drug delivery system which itself and its degradation products are compatible with the human body.

Another object of the instant invention is to provide a backbone polymer or carrier which is hydrolyzable, i.e. biodegradable.

Another object of the instant invention is to provide a bioactive compound via covalent bonding to a polymeric backbone so that upon hydrolysis of said covalent bond said bioactive compound is released in active, unmodified form.

SUMMARY OF THE INVENTION

A time-release chemical delivery system for delivering bioactive agents from an implant site within an animal has been invented. The system comprises a polymeric biodegradable carrier and a bioactive compound attached to the carrier by a hydrolyzable bond. The carrier may be a homo-polymer or copolymer and is preferably a polymer such as a polyester, polycarbonate, polyamide or polyurethane which slowly degrades within its host without producing extremely toxic degradation products. The bioactive compound may be any compound which can be attached covalently, that is, by a hydrolyzable bond, to the carrier polymer, either directly or indirectly through a chemical space unit.

The delivery system is usually implanted subcutaneously by injection or incision in an animal, including the human body. A hydrolyzable carrier, such as high molecular weight polymers, is desirable since they are not easily dissolved or absorbed by the body and remain at the implantation site until the bioactive compound has been substantially released. However, the carrier polymer of this invention ultimately hydrolyzes to degrade into smaller chemical compounds which are easily absorbed and ultimately substantially completely dissipate from the implantation site. Also, in very high molecular weight polymers, hydrolysis of the polymer backbone may be a factor in the time release of the bioactive chemical. Generally, however, the rate of hydrolysis of the bioactive compound covalent bond to the polymer will be greater than the rate of hydrolysis of the polymer.

POLYMERIC BIODEGRADABLE CARRIER

As indicated heretofore, the carrier is biodegradable and produces degradation products which are biologically compatible with the host. The time-release chemical delivery systems of this invention are intended for implantation, either surgically or by injection in animals, including humans. A polymeric carrier which does not degrade are much less desirable for use in implants since the implanted device should be later surgically removed. Also, polymers which degrade into toxic substances are not desirable for this purpose. Also, highly water soluble polymers are generally not desired inasmuch as immediate absorption into the host may create toxicity problems and the absorption rate may become the controlling factor in the release of the bioactive compound. The carrier polymer of this invention preferably remains at the implantation site until a substantial quantity of the bioactive compound has been released.

The polymeric biodegradable carriers of this invention are ones which have hydrolyzable bonds, for example, an ester, amide or urethane bond, such as those found in condensation polymers. A further requirement of the polymeric carriers are that they contain a pendant group to which a reactive compound may be directly attached by a hydrolyzable bond or to which a spacer unit may be attached with the reactive compound attached to the spacer unit by a hydrolyzable bond. Typically, the space unit will also be attached to the polymeric carrier by a hydrolyzable bond.

Typical polymeric carriers are polyesters, polyamides, polyurethanes and other condensation polymers having a molecular weight between about 5,000 and 1,000,000. The molecular weight may be utilized to influence the rate of release of the reactive compound, for example, higher molecular weight polymeric carriers may present more resistance to hydrolysis and thus retard the release of bioactive agents while a very low molecular weight carrier would be more easily hydrolyzed and increase the release of bioactive agents. In some instances, it may be desirable to admix time release delivery systems made with high molecular weight carriers with those made from low molecular weight carriers to alter the effective rate of release of materials.

A preferred condensation polymer has been prepared for the above purpose from -L-glutamic acid, a naturally occurring amino acid. The resulting polymer is hydrophilic and biodegradable. L-glutamic acid is reacted according to the following diagram with benzyl alcohol to form gamma-benzyl-L-glutamate. Gamma-benzyl-L-glutamate is then reacted with phosgene to form the N-carboxyanhydride which is then reacted in the presence of triethyl amine in an inert solvent, for instance, benzene and dichloromethane to form poly(gamma-benzyl-L-glutamate).

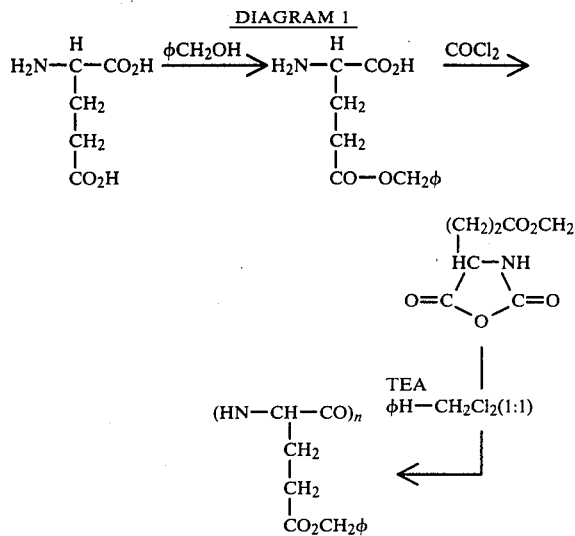

DIAGRAM 1

The poly(gamma-benzyl-L-glutamate) is then reacted in the presence of a mixture of hydrogen bromide and hydrogen chloride to form poly(L-glutamic acid). The poly(gamma-benzyl-L-glutamate) can also be reacted with an hydroyalkyl amine to form poly(hydroxyalkyl glutamines).

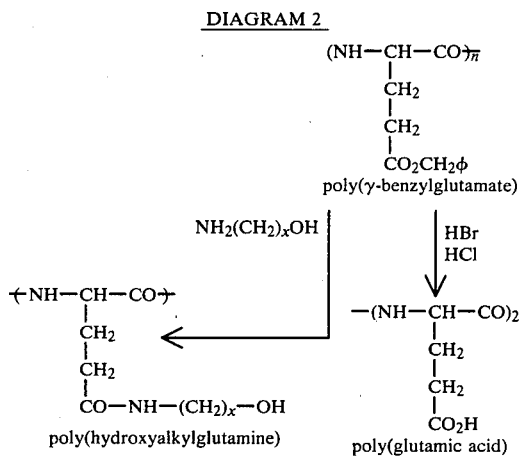

DIAGRAM 2

Poly(L-glutamic acid), poly(hydroxyalkyl-l-glutamines) and poly(-L-aspartic acid), and poly(hydroxyalkyl-L-aspartic acid) have pendant reactive groups. In the case of poly(-L-glutamic acid), the reactive group is a carboxylic group while in the case of poly(hydroxyalkyl glutamines) the reactive group is a hydroxyl group. In viewing the large number of reactive sites present on these polymers, it is apparent that it may not be possible to react each pendant reactive group with a bioactive compound especially if the bioactive compound is a bulky molecule which causes steric hindrance to reaction at adjacent pendant groups. Thus, it may be desirable to introduce spacer groups on the polymer chain which diminish the steric hindrance and allow the increase of the percentage of drug loading.

The use of a spacer group may also provide desirable changes in drug release rate by allowing ease of hydrolysis of the drug. If the drug is further removed from the main chain it would be less influenced sterically by the polymeric backbone.

Depending upon the aqueous solubility of the bioactive agent, the polymeric carrier must be altered to achieve an optimum release rate. For example, for delivery of hydrophilic drugs, the polymeric backbone must be made hydrophobic. Of course, the opposite is also true. That is, for hydrophilic drugs, the polymeric backbone might be made hydrophilic in order to achieve an optimum rate of drug release. The polymer can be diminished in hydrophilicity or even made hydrophobic by the incorporation of amino acids, such as L-alanine, L-leucine and L-valine, into the polymer backbone yielding a variety of copolymeric systems. Since these hydrophobic L-amino acids have no side chain carboxyl or hydroxyl group, the hydrophilicity of the polymer is reduced. The reaction of L-glutamic acid with L-valine is illustrated in the following diagram.

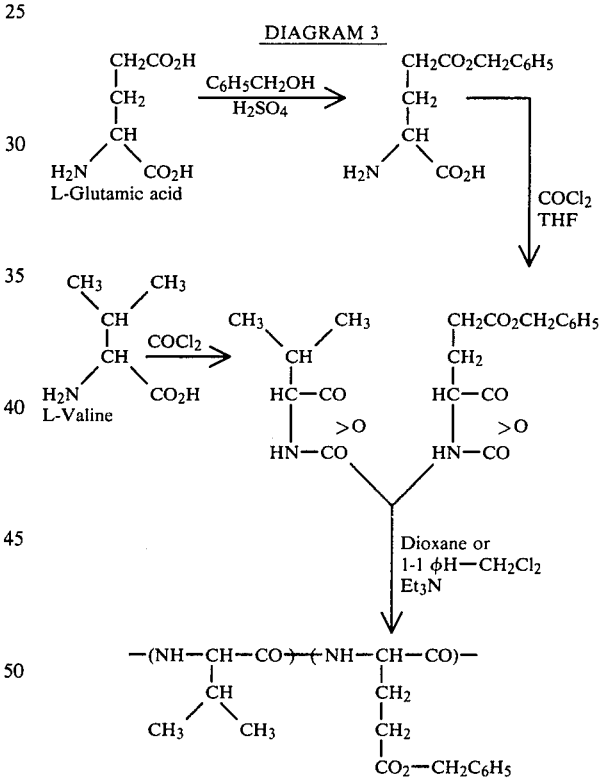

DIAGRAM 3

Other condensation polymers which may be utilized for implantation purposes as a carrier in a time-release system for delivering a reactive compound systemically to an animal include homopolymers and copolymers having amide, ester, carbonate and urethane linkages.

The number of polymers in the class called condensation polymers is very large. In theory, all of these polymers plus other polymers that have a pendant group for drug attachment and shown an appreciable note of biodegradation within an animal host can be used as the drug carrier. The only limitations for the polymeric drug carrier is that it must be biodegradable in a finite period of time, say five years or less, and that the degradation products must be biologically compatible with the host at their release concentration. Most polymers in the above class which contain a pendant group cannot be prepared directly, but must be prepared (1) by protection of the pendant group (called masking) during polymerization, after which the group is deprotected or chemically modified to yield the reactive pendant group, or (2) by post-polymer reaction to chemically yield the reactive site. Examples of both type reactions are listed on the following page.

EXAMPLE 1

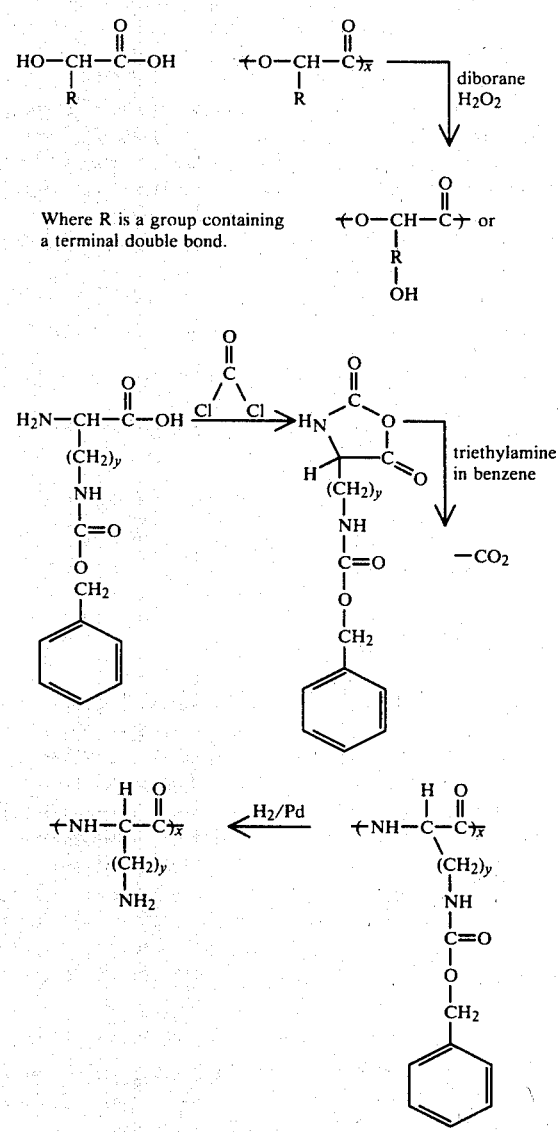

EXAMPLE 2

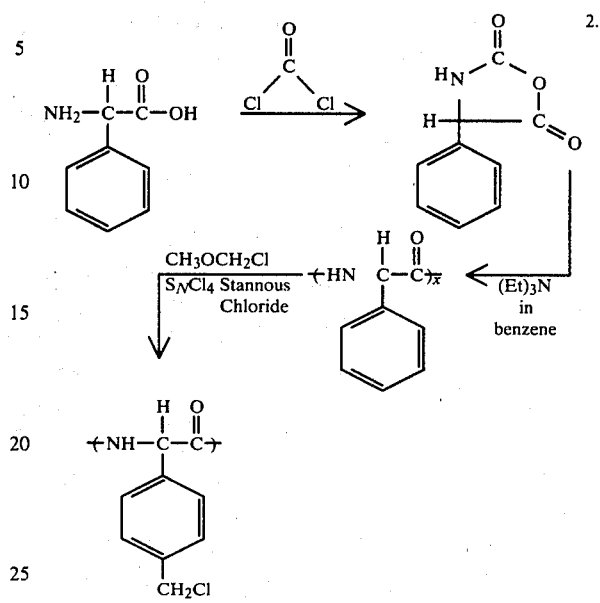

Preferred condensation polymers are those prepared from naturally occurring dicarboxylic -L-amino acids. Since such naturally occurring amino acids are not foreign to an animal host, the least possible toxicity should be encountered.

The preferred naturally occurring L-amino acids are aspartic acid

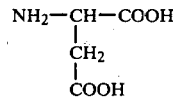

and L—glutamic acid

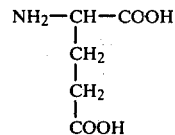

each of which have the pendant carboxyl group close to reactive amino group. Polymers formed from L-aspartic acid and L-glutamic acid thus have the pendant —COOH group close, no more than two linear carbon atoms spacing, to the polymer backbone. Since the proximity of the reactive carboxyl group to the polymer backbone may interfere with the addition of a bioactive compound, especially a large molecule, and with the subsequent hydrolysis of a covalent bond formed by such condensation reaction, the use of a spacer group, preferably linear in nature, may be preferred in this invention.

PENDANT REACTIVE SITES

To be effective as hydrolyzable carriers the polymers of this invention must have pendant reactive sites to which a bioactive compound may be attached. The term bioactive compound has the connotation that it is active for some purpose in the host in which the time release delivery system is implanted. Preferred pendant reactive sites in this invention are carboxyl, hydroxyl, amino, sulfhydryl, sulphate, and phosphate groups. These functional groups may react with functional groups of the bioactive compound to form a hydrolyzable bond. The hydrolyzable bond may be direct between the pendant group of the polymer and the reactive compound or it may be first reacted with a spacer unit which contains a similar reactive functional group.

The reactivity and density of reactive sites may be affected by incorporating monomeric units into the polymer chain which have no pendant reactive sites.

The reactivity of the reactive sites is also affected by the distance of the reactive site from the backbone of the polymer. In poly(L-glutamic acid) the reactive carboxyl site is spaced by two carbon groups from the polymer backbone. The use of poly(hydroxyethyl-L-glutamines) places the reactive group six carbons from the polymer backbone. Thus, a synthetic amino acid having a longer chain between the amine group and the carboxyl group could be utilized in place of an intermediate spacer group. These have generally not been preferred inasmuch as such dicarboxylic L-amino acids are not found in nature.

SPACER GROUPS

Spacer groups may be utilized in the practice of the instant invention to provide a hydrolyzable unit which spaces the reactive compound further from the carrier backbone. As indicated hereinabove, the polymeric units may contain long pendant chains which place the reactive site on the pendant group further away from the carrier backbone. However, when the carrier backbone hydrolyzes, the monomeric unit can have a rather substantial size and thus must be compatible with the host. Smaller monomeric units such as glutamic acid and aspartic acid should be more easily handled by biological systems. Particular spacer units which have been used in this invention are hydroxyalkyl amines, i.e., alkanolamines, such as ethanolamine and propanolamine. These low molecular weight hydroxyalkyl amines, when hydrolyzed, are released into the animal system and are compatible therewith. Also, these type spacers provide a reactive site, namely a hydroxyl group, for attachment by the reactive compound.

BIOACTIVE COMPOUNDS

Bioactive compounds useful in this invention are those which contain a group which may react to form a bond with a pendant group or a spacer group. The bond is preferably hydrolyzable and in particular are esters, including sulfates or phosphate esters, amides, carbonates and urethane bonds. A class of bioactive compounds particularly useful in this invention are progestins. The time release chemical delivery system is thus useful in animals, including humans, as a contraceptive delivery system. One particular progestin useful in norethindrone which has the following formula.

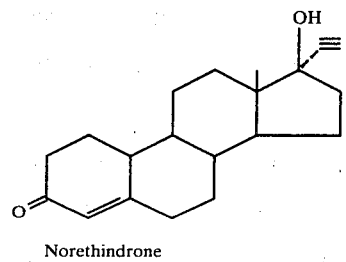

Norethindrone

The reactive hydroxyl group of norethindrone may be reacted with phosgene. A phosgene treatment converts the 17B-hydroxyl group to a chloroformate

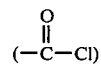

group, which is then reacted with the hydroxyl group of the polymer to form a carbonate linkage between the polymer and the norethindrone.

The reactive compound which is released over a period of time in the instant invention may be one which has a pharamacological affect upon the host, for example, a contraceptive drug in an animal. During drug release the polymer degrades into small fragments which are easily handled systemically by the host. Thus, shortly after the last of the drug has been released into the animal's system the polymeric residue also degrades to leave no residue at the implantation site.

Factors which affect the release rate and the rate of absorption into the body of the host include the size of the particles, the total molecular weight of the polymer, the composition of the polymer backbone, the length and character of the spacer groups and the character of the pendant groups and the degree of loading, that is, the percentage of available pendant reactive sites from the polymer which are reacted with the bioactive agent. The drug or other biologically active agent which is carried by the polymer may be hydrophobic in nature while the polymer is hydrophilic. When the drug is very hydrophilic, the hydrophilicity of the polymer spacer system must be adjusted to prevent dissolution of the drug delivery system. The spacing of the bulky drug or chemically reacted compound from the polymer also affects the rate of release.

POLYMER SYNTHESIS

Poly-gamma-benzyl-L-glutamate was prepared by the polymerization of N-carboxy-gamma-benzyl-L-glutamate anhydride[1,2] in dioxane using triethylamine as initiator. The degree of polymerization was determined from viscosity measurements in trifluoroacetic acid.

[1] W. E. Hanby, S. G. Waley and J. Watson, J. Chem. Soc., 3239 (1950).
[2] E. R. Blout, and R. H. Karlson, J. Am. Chem. Soc., 78, 941 (1956).

The resulting polymer was dissolved in dioxane (2 g/ml) and an excess of 3-amino-1-propanol was added (8 ml/g of polymer). Stirring continued at 60° C. for 20-40 hours until a clear solution was obtained and a sample of the reaction mixture gave no precipitate in water. The polymer was precipitated in 5 volumes of chloroform and dried. The polymer was dissolved in water and dialyzed to remove low molecular weight material. The water was removed under vacuum to give the glassy polymer in approximately 90% yield.

POLYMER-STEROID COUPLING REACTOR

To a solution containing 200 mg norethindrone, 15 ml freshly distilled methylene chloride, and 0.120 ml pyridine was added 14 mls of a 20% phosgene in benzene solution. After 1½ hours, a good yield of norethindrone-17 beta-chloroformate results. If tritiated norethindrone is used in the reaction, 91% of the activity on thin layer chromatography (TLC) corresponds to the chloroformate (Rf. 0.09 for norethindrone, Rf. 0.32 for norethindrone-17 beta-chloroformate using Quantagram Q5F TLC plates developed in 1% ethanol in chloroform. The reaction mixture was evaporated to dryness under reduced pressure.

During the above procedure, 120 mg of dry poly(hydroxypropyl glutamine) was dissolved in 3 ml of anhydrous dimethyl formamide and 1 ml of anhydrous pyridine. This solution was added to the norethindrone-17 beta-chloroformate reaction vessel and allowed to react for four hours at room temperature. The reaction product was isolated by precipitating into 100 ml ethyl acetate. The precipitate was redissolved in 2 ml of dimethyl formamide and reprecipitated into 100 ml ethyl acetate. The product was dried in vacuum to yield approximately 0.165 mg of norethindrone coupled polymer. When tritiated norethindrone was used in reaction, liquid scintillation counting techniques reveals that up to 64% of the available hydroxyl groups of the polymer are coupled with norethindrone.

EXAMPLE I

In the following example compound XXb is frequently referenced. Compound XXb has the following formula:

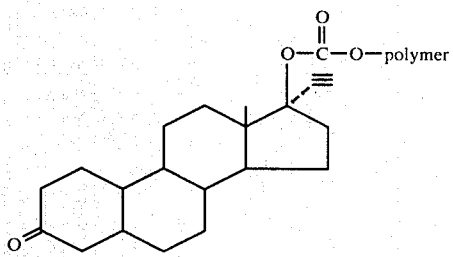

The polymer is poly(hydroxylpropyl-L-glutamine) having an average molecular weight of 53,000 as determined by viscosity and 33% to 55% of the available pendant hydroxyl groups reacted with norethindrone.

Infrared spectrum of the product, XXb, shows peaks at 1760 cm$^{-1}$ (carbonate), 1660 cm$^{-1}$ and 1550 cm$^{-1}$ (amide) and 3300 cm$^{-1}$ (hydroxyl). The nuclear magnetic resonance (NMR) spectrum of the product shows that the 18-methyl group of norethindrone is shifted to 0.97 delta, typical of the norethindrone carbonate. The degree of substitution as determined using tritiated norethindrone and scintillation counting techniques ranges from 33% to 55% in various batches.

In Vivo Pharmacokinetic Studies

Two batches of the polymer $^3$H-XXb (Batch No. A and B) were administered to rats in order to determine the in vivo releasing rate of norethindrone from the polymer. The general procedure for the in vivo kinetic study is as follows.

The polymer-Batch No. A (5 mg XXb/1.75 mg norethindrone/7.4×10$^6$ dpm or 10 mg XXb/3.9 mg norethindrone/1.5×10$^7$ dpm) or Batch No. B (10 mg XXb/4.9 mg norethindrone/2.92×10$^7$ dpm) was accurately weighed and placed in normal saline (5 ml) overnight. The next morning, the supernatent was decanted off leaving only the wetted polymer.

A mature female Sprague-Dawley rat weighing 220-260 g. was anesthetized with ether. An incision about 2 cm. in length was made on the dorsal side of the neck and upper thorax to expose the area just below the skin in the subcutaneous tissue. The polymer containing tritiated norethindrone (XXb) was placed into the subcutaneous area and the incision was closed. Care was taken so that no hemorrhage occurred at the site of implantation. The incision area was kept as sterile as possible during the whole procedure of implantation. The rat with implanted polymer was plaed into a metabolism unit and the feces and urine was collected on a daily basis for at least 10 days following the administration of the compound. Thereafter, the biological samples were collected on Mondays, Wednesdays, and Fridays.

The total volume of urine was measured and 1 ml. aliquot of urine was sampled. To the urine sample 12 ml. of NEN Formula 950 A Scintillation Cocktail was added and the sample counted for radioactivity. The total amount of fecal matter for each collection period was pooled, weighed, and put in an oven at 60° C. for about 12 hours until dry. The dry mass was then pulverized to a homogenous mixture of fine powders in a blender. Aliquots of the dried fecal matter (0.2-0.3 g) was placed in a glass scintillation vial and 0.2 ml. 70% perchloric acid and 0.4 ml. hydrogen peroxide were added. The mixture was incubated for 8-12 hours at 60° C. in a shaking water bath for 4 to 8 hours until all the fecal matter was completely dissolved. After the digestion, the vials were cooled for 30 minutes at room temperature before adding 12 ml. of NEN Biofluor Scintillation Cocktail. The vials were then kept in a dark place for at least 24 hours before counting in a Beckman 9000 Scintillation Counter.

The total amounts of radioactivity excreted in the urine and feces, as well as the sum of these two, which represents in a steady state the in vivo releasing rate of radioactivity from the polymer, were determined for each rat. The present procedure yields counting efficiency ranging from 15-25% for fecal samples.

(1) Batch A

The in vivo releasing rate of $^3$H-norethindrone from Batch No. A preparation was determined after the subcutaneous administration of the preparation in two female rats. The first rat was injected with 4.9 mg XXb/1.0 mg norethindrone/7.4×10$^6$ DPM while the second rat was injected with 10 mg XXb/3.9 mg NE/1.5×10$^7$ DPM. The rats were continuously monitored throughout this period and the total radioactivity excreted in the urine and feces was measured. Both rats were found to excrete a rather constant amount of radioactivity per day all throughout this period of 268 and 341 days. During the first 20 days the amount of norethindrone released gradually increased to an amount of 25 micrograms per day. Thereafter, it gradually dropped to an amount of about 2.5 micrograms per day at the fiftieth day. The amount of norethindrone released gradually dropped to about 1.2 micrograms per day at the 160th day. The amount of norethindrone released by the second rat was larger per day than for the first rat with an average release of about 3 micrograms per day between the 70th and 140th day. It is estimated that the releasing rate of norethindrone from Batch No. A in vivo is about 0.5 microgram norethindrone/mg XXb/day.

(2) Batch B

A result similar to the one obtained with Batch No. A was observed with Batch No. B in five rats. The average releasing rate of this particular batch was about 0.65 micrograms norethindrone/mg polymer/day up to 35 day post implantation. A gradual decline was thereafter noted through day 136. A minor spur in the release of radioactivity was found with this preparation immediately following the administration. The release rate, however, quickly reached a trough at day five and then gradually attained the plateau value around day 11.

The in vivo results obtained with Batch No. A and B are most encouraging. These data demonstrate that a rather sustained zero-order releasing rate of norethindrone can be achieved with compound XXb.

We claim:

1. A time release chemical delivery system for implantation in animal host comprising:
    a polymeric, water-insoluble, biodegradable polymer which biodegrades into fragments tolerable by the host; and
    a bioactive compound chemically attached to said carrier by a hydrolyzable bond, said bioactive compound containing a group which reacts with a group on the biodegradable polymer to form a hydrolyzable bond and being effective in small dosages to produce a biological effect within said host upon release into the host by hydrolysis of the hydrolyzable bond.

2. The chemical delivery system of claim 1 wherein said polymer is a condensation polymer having reactive pendant groups.

3. The chemical delivery system of claim 1 wherein said polymer has a molecular weight of about 5,000 to about 1,000,000.

4. The chemical delivery system of claim 1 wherein said polymer is a polymer or copolymer of glutamic acid or aspartic acid.

5. The chemical delivery system of claim 2 wherein at least one percent (1%) of said reactive pendant sites are coupled to a reactive compound.

6. The chemical delivery system of claim 1 wherein said bioactive compound is indirectly coupled to said carrier by a hydrolyzable bond to a spacer compound.

7. The chemical delivery system of claim 6 wherein said spacer is substantially a linear compound.

8. The chemical delivery system of claim 7 wherein said spacer compound is coupled to said bioactive compound by a hydrolyzable bond.

9. The chemical delivery system of claim 2 wherein the carrier is a polyester, polyamide or polyurethane polymer.

10. The time release chemical delivery system of claim 1 wherein said hydrolyzable bond is an ester, amide or urethane bond.

* * * * *

UNITED STATES PATENT OFFICE
CERTIFICATE OF CORRECTION

Patent No. 4,356,166  Dated October 26, 1982

Inventor(s) Robert V. Petersen, et al

It is certified that error appears in the above-identified patent and that said Letters Patent are hereby corrected as shown below:

In the "inventors" section:
    add ---Sen-Maw Fang, Salt Lake City, Utah ---;
    change "Robert V. Peterson" to
    ---Robert V. Petersen---;
    change "Sunj-Wan Kim to
    ---Sung-Wan Kim---;

Col. 2, line 49, change "space" to ---spacer---;

Col. 10, line 16, change "plaed" to ---placed---.

Signed and Sealed this

Twenty-ninth Day of March 1983

[SEAL]

Attest:

GERALD J. MOSSINGHOFF

Attesting Officer     Commissioner of Patents and Trademarks